US00RE34373E

United States Patent [19]

Collins et al.

[11] E Patent Number: Re. 34,373

[45] Reissued Date of Patent: Sep. 7, 1993

[54] MICROWAVE HEATING APPARATUS FOR LABORATORY ANALYSES

[75] Inventors: Michael J. Collins, Charlotte; Dennis P. Manchester, Matthews, both of N.C.

[73] Assignee: CEM Corporation, Matthews, N.C.

[21] Appl. No.: 704,774

[22] Filed: May 23, 1991

Related U.S. Patent Documents

Reissue of:

[64] Patent No.: 4,835,354
Issued: May 30, 1989
Appl. No.: 189,727
Filed: May 3, 1988

U.S. Applications:

[63] Continuation of Ser. No. 31,906, Mar. 30, 1987, abandoned, which is a continuation of Ser. No. 416,011, Sep. 8, 1982, abandoned.

[51] Int. Cl.[5] ..... H05B 6/78

[52] U.S. Cl. ..... 219/10.55 B; 219/10.55 F; 219/10.55 R; 333/22 F

[58] Field of Search ..... 219/10.55 B, 10.55 R, 219/10.55 A, 10.55 D, 10.55 F, 10.55 E; 392/356; 333/22 R, 22 F; 374/149

[56] References Cited

U.S. PATENT DOCUMENTS

| | | | |
|---|---|---|---|
| 2,716,694 | 8/1955 | Schroeder | 219/10.55 R |
| 3,463,894 | 8/1969 | Bleackley | 219/10.55 A |
| 3,566,066 | 2/1971 | Borthwick | 219/10.55 R |
| 3,673,370 | 6/1972 | Johnson | 219/10.55 A |
| 3,676,058 | 7/1972 | Gray | 219/10.55 R |
| 3,806,837 | 4/1974 | Carr et al. | 219/10.55 |
| 3,973,101 | 8/1976 | Bosse | 219/356 |
| 4,115,678 | 9/1978 | Tachikawa et al. | 219/10.55 B |
| 4,158,759 | 6/1979 | Mason | 219/10.55 B |
| 4,210,795 | 7/1980 | Lentz | 219/10.55 B |
| 4,255,639 | 3/1981 | Kawabata et al. | 219/10.55 B |
| 4,276,462 | 6/1981 | Risman | 219/10.55 F |
| 4,308,445 | 12/1981 | Offutt | 219/10.55 F |
| 4,517,430 | 5/1985 | Slottag | 219/10.55 B |
| 4,625,089 | 11/1986 | Gics | 219/10.55 R |

FOREIGN PATENT DOCUMENTS

| | | | |
|---|---|---|---|
| 56-49821 | 5/1981 | Japan | 219/10.55 B |

*Primary Examiner*—Philip H. Leung
*Attorney, Agent, or Firm*—Raymond F. Kramer

[57] ABSTRACT

A microwave oven particularly suitable for laboratory analytical use is described. The oven is designed for chemical digestion and the drying of materials to very low moisture levels. The oven utilizes a rotating platform to move the material being subjected to microwave radiation through the oven chamber to ensure uniform contact of the microwaves with the material. Radiation mixers and radiation isolators are also used to disperse radiation in the oven and absorb excess radiation.

11 Claims, 2 Drawing Sheets

MICROWAVE HEATING APPARATUS FOR LABORATORY ANALYSES

Matter enclosed in heavy brackets [ ] appears in the original patent but forms no part of this reissue specification; matter printed in italics indicates the additions made by reissue.

This is a continuation of application Ser. No. 07/031,906 filed Mar. 30, 1987 which is a continuation of application Ser. No. 06/416,011 filed Sept. 8, 1982, now both abandoned.

This invention relates to an apparatus for the microwave drying and chemical digestion of materials for laboratory purposes. More particularly, the invention is directed to a microwave oven particularly suitable for analytical laboratory usage such as for the rapid drying of material to extremely low moisture levels and the rapid chemical digestion of materials as is desirable for analytical and laboratory purposes.

BACKGROUND OF THE INVENTION

Microwave ovens have come into common usage primarily for the heating and cooking of food for human consumption. Various other uses have also been developed. For instance, the microwave oven has been found to be particularly suitable for the rapid drying of various substances and determination of volatile content such as is set forth in U.S. Pat. No. 3,909,598. Further, it is known that microwave radiation greatly enhances the chemical digestion of various materials either as a result of the molecular stimulation caused by microwave radiation and/or the heating effect. Methods which use microwave radiation in acid digestion are also known.

Various developments in microwave oven technology have included the ability to program the oven to control the power input/output of the magnetron as well as the length of time that the magnetron will run. However, because most of these designs have been directed to ovens which maximize the energy input into the substance being heated such as is required for cooking, such ovens are not suitably designed for laboratory usage.

In laboratory usage, many analytical methods require the reduction or elimination of moisture in a sample, or at least, reduction to a very low near complete dryness. This makes conventional microwave ovens unsuitable for many analytical methods. As moisture level in a sample subjected to microwave oven heating is reduced to low levels, excessive radiation energy is reflected from the oven as it can no longer be absorbed by the sample. The loss of the polar absorbing material in the sample causes the microwaves to be reflected back to the magnetron. Such reflected radiation quickly damages the magnetron.

Further, due to the characteristics of microwave radiation, it is diffucult even under ideal mechanical and size configurations based on wave length, to thoroughly disperse the radiation throughout an oven to provide uniform heating. Typical microwave ovens are best suitable for the placement of relatively large packages to be heated within the oven thereby taking up a relatively large percentage of the oven capacity. With analytical laboratory usage, normally relatively small samples are used, thus taking up a very small percentage of the oven cavity. When small samples are used, excess radiation has inadequate polar material to absorb the energy and the wave energy is thus reflected back to the source i.e., the magnetron. Also, hot spots frequently develop in the sample which may destroy part of the sample. For most cooking purposes, localized hot spots are of little significance because they in turn aid in convection and conductive heating of the rest of the package notwithstanding the localized heating to higher temperatures in various portions of the package. Such irregular heating and the development of hot spots is particularly unsuitable for laboratory usage.

THE INVENTION

In accordance with the invention, a microwave oven particularly suitable for analytical laboratory usage is provided comprising an enclosure forming a chamber for the retention of microwave radiation, said enclosure having means communicating therewith for dispersing microwave radiation throughout said chamber, means for absorbing excess microwave radiation, means for removing volatiles from said chamber and means for moving items in the said chamber while being subjected to microwave radiation, said microwaves being directed into said chamber from a magnetron, said magnetron power input, duration of power input, volatile removal means and moving means in said chamber being controlled to interact with each other as selectively programmed prior to operation. The preferred apparatus utilizes a turntable positioned in said chamber which preferably forms an oven and said turntable slowly rotates in the chamber during the application of microwave energy.

DETAILS OF THE INVENTION

The present apparatus provides the ability to reduce the moisture content of a sample for analytical purposes to less than one tenth of a milligram of water without danger of damaging the magnetron of the microwave oven. Samples of extremely small size, on the order of less than one gram up to the capacity of the oven, can be effectively utilized while providing substantial improvements in even heating. The oven utilizes a rotatable turntable for placement of the sample which results in the sample being passed throughout the oven as it is radiated. This avoids a fixed location which may result in excessive or inadequate radiation. In addition, the microwave oven utilizes radiation dispersing means and radiation isolator means. These modifications result in a microwave oven which is totally transparent to microwave radiation and can be safely operated with a zero load, i.e., empty oven cavity, without danger of magnetron damage.

BRIEF DESCRIPTION OF THE DRAWING

The invention will be more readily described by reference to the drawing, wherein.

Figure 1:
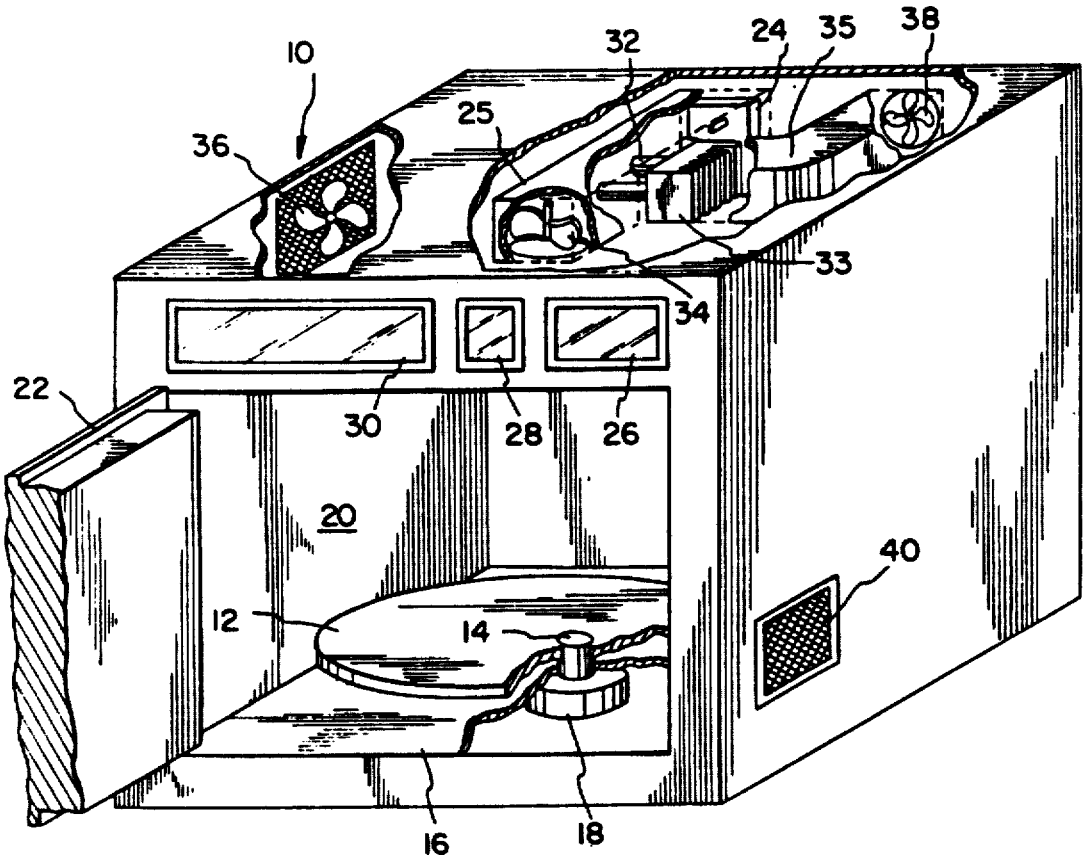
FIG. 1 is a partially cutaway perspective view of the analytical microwave apparatus of the present invention.
Figure 3:
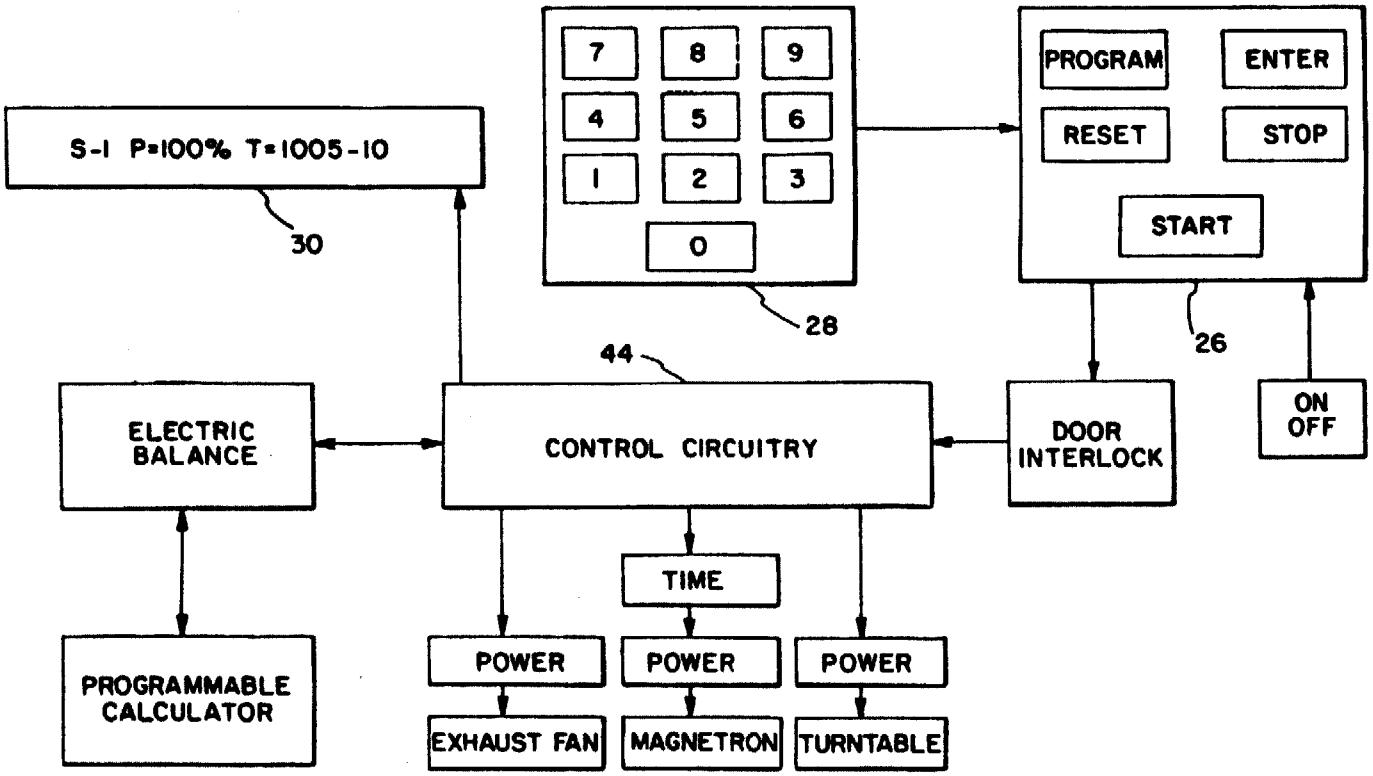
FIG. 3 is an elevational view of control panel parts identified by numerals 26, 28 and 30 of FIG. 1, and a block diagram of associated circuitry for controlling the invented apparatus.
Figure 2:
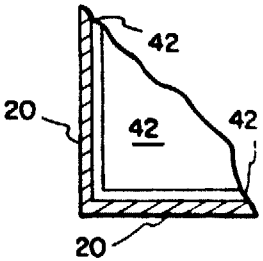
FIG. 2 is a cutaway view of the interior sidewalls of the microwave apparatus of the invention.

The apparatus of the present invention comprises a microwave oven 10 specifically adapted for the purpose of reducing volatile content to a very small residual. A conventional microwave oven 10 is modified to provide a rotatable turntable 12 which is transparent to microwave radiation. Polypropylene, Teflon, polycarbonates, polyester and the like plastics are preferably used for the turntable 12 and axle 14. Turntable 12 is fixed to an axle 14 which extends through the floor 16 of microwave oven 10. Axle 14 is driven by motor 18 which can be of variable speed or of fixed geared ratio to provide the desired turning speed. It is preferable to have a variable speed turntable because it has been found that certain processes for which the present invention is particularly suited are responsive to different rotational speeds. Thus a speed which is best suited for the chemical digestion or drying operation can be selected to give the most desired result.

The microwave oven may be of conventional design having the modifying improvements set forth herein added thereto along with proper radiation shielding. The modifications particularly needed for the present contemplated uses are a radiation mixer 34 to mix and disperse the radiation. Various radiation mixers are known and have been described in the art. Normally they are rotating fan-like machines which reflect the radiation. Such mixers reduce the production of hot spots which could decompose or destroy part of the sample being tested. The radiation mixer 34 is positioned between the magnetron 24 and the chamber forming the oven to thereby disperse the radiation as it enters the oven chamber.

The internal chamber of microwave oven 10 comprises floor 16, sidewalls 20, ceiling (not shown) and door 22. These internal parts can be coated with chemically resistant finishes 42, such as ceramic, Teflon, epoxy and the like to increase their life for use with corrosive materials. Door 22 is provided with safety switches which ensure that magnetron 24 cannot be operated without the door being in the closed and sealed position. Such safety devices are well known and required by Federal regulations to avoid the loss of radiation from the oven.

Magnetron 24 is located preferably outside of the oven chamber and uses a wave guide 25 to direct the microwave radiation into the oven proper. Alternatively, magnetron 24 can be positioned within the oven chamber itself to provide correspondingly good results. However, the dimensional size of the oven is thereby further limited to a factor of the wave frequency and thus the utilization of the wave guide to direct the radiation into the oven proper is normally preferred.

The oven magnetron 10 is preferably of standard manufacture having a power output of 500 to 800 watts and a frequency within government approved ranges. The operator can control the power of the magnetron within the limits of 0 to 100 percent power input in one percentage point increments. The United States Federal Communication Commission has designated the frequencies of 915 and 2450 megahertz as suitable for microwave oven magnetrons. Larger or smaller magnetrons could be used with corresponding limitations in versatility. Larger magnetrons are generally unnecessary with 600 watt magnetrons being found to be quite suitable for analytical usage of the present invention.

The magnetron is conventionally located exterior of the oven chamber, but it could in fact be in the oven chamber. In such instances, a wave guide forms the oven chamber with the magnetron being positioned at one end. However, conventional usage has indicated a preference for mounting the magnetron exterior of the oven chamber and utilizing a wave guide 25 to direct the radiant energy into the chamber. In all instances, adequate radiation shielding is provided to avoid leakage of radiation from the instrument as is required by government regulations. Additionally, safety interlocks are provided to eliminate the possibility of the magnetron being activated when the oven or chamber door is not completely closed.

Microwave oven 10 is controlled by programmable microprocessor or mechanical timers, power control switches and the like devices which provide the ability to vary the microwave intensity during drying or heating cycles as well as the time of such cycles. Microwave oven 10 is thus provided with control panel 26, numerical input panel 28 and digital readout panel 30. In the operation of the oven 10, control panel 26 provides for setting the program, entering a new program, resetting the program, starting and stopping the program. Numerical input panel 28 provides for selectively choosing numerical input for the operation of the microwave oven. Digital panel readout 30 provides visible numerical reading of the program in operation including the percentage power of the magnetron, the time of the program and the stage of the program.

In addition to the radiation mixer 34, the oven is equipped with radiation absorbing material or isolators 32. Radiation absorbing materials will couple with the radiation being emitted in the oven thus preventing decomposition of the sample due to excess radiation particularly as the amount of polar substances decrease in the sample thus limiting the amount of absorption in the sample. By having a radiation coupling material present, the life of the magnetron is greatly increased. Further, such coupling material additionally helps in preventing leakage of radiation from the oven.

It has been suggested that coupling materials such as water be used, although any other polar substance could be used. The polar substance is circulated through the oven in radiation transparent tubing. The amount of coupling material used in this way can then be readily regulated and adjusted to the desired volume. In one method of use, a loop of radiation transparent tubing is conveyed through the oven flooring or sidewalls from a reservoir. The temperature rise created by the absorption of radiation will effect the circulation of the water through the tubing from the reservoir. While this method can be used to protect the magnetron, it has the particular disadvantage that the coupling material due to its mass competes for the radiation energy in the oven and can in effect greatly hinder the heating of a small sample. The undesirable effects of radiation being absorbed by the coupling agent become even more pronounced in attempting to heat a small sample to near total dryness. The preferential absorption of the radiation by the larger mass of the coupling material will often defeat the attempts to dry the sample.

Rather than utilizing a coupling material such as water or other polar substance, a radiation isolator 32 can be used. An isolator is a device which preferentially absorbs reflected radiation and prevents damaging reflection back to the magnetron.

In the present invention, the radiation isolator 32 is located between the magnetron 24 and the oven chamber such as in the wave guide 25. Radiation isolators 32 are commercially available devices which comprise magnetic shapes coupled wit heat sinks. The isolators are designed to permit originating microwaves emitted from the magnetron 24 to pass through the isolator unaffected. Reflected waves, however, are absorbed by the isolator and converted to heat energy. The isolator 32 in fact has a propensity to attract reflected radiation and thus will actually tend to draw the reflected radiation out of the oven chamber.

Isolator 32 converts the reflected radiation into heat which is dissipated through isolator heat exchanger 33. Heat exchanger duct 35 communicates with heat exchanger 33 and fan 38 which draws off the produced heat. Fan 38 and isolator heat exchanger 33 are selected to be of sufficient capacity to absorb the full capacity of magnetron 24 reflected energy with a zero oven load for prolonged, indefinite operation. This ability to operate the oven with a zero load enables the present invention to rapidly and effectively concentrate the microwave energy on any given sample size, even those with very low polar material present. Total drying can be effected without damage to the magnetron and without use of competing radiation absorbers being present in the oven. The total microwave transparency of the oven itself further prevents the heating of the oven itself which can be detrimental to continuous sample testing.

In addition to the noted isolators and radiation mixers, exhausting means 36 is provided for the removal of vapors from the oven. Air intake panel 40 is provided to draw a flow of air through the oven. The control of air flow through the oven can be important particularly in drying processes wherein large quantities of volatiles are being expelled. For chemical digestion uses, high volumes of air may be desirable to remove fumes which are given off in the digestion. Thus, a programmable or variable speed exhaust fan is provided, the speed of which can be regulated by the power supplied to the fan motor. Alternatively, the fan speed can be simply controlled by manual setting by the operator. The speed of the fan and corresponding air flow can be critical to the desirable operation of the invention. When large volumes of volatiles need to be removed, high air flows greatly enhance volatilization. When light power-like materials are being treated, low air flow rates will prevent the loss of sample material from the sample plate.

In the operation of the oven, the operator selects the magnetron power to be utilized, the time of operation and the volume of air flow through the chamber. In addition, the speed of the rotation of the turntable 12 within the desired ranges of about one-half revolution per minute to about twenty revolutions per minute can be optionally selected. For most usages, however, the turntable rotation can be preset with about one revolution per minute being adequate for most purposes to avoid the development of hot spots in the sample being radiated.

The preferred method of controlling the apparatus is by means of a microprocessor 44, wherein the operator programs the sequence of operation directly into a reprogrammable processor which is part of the oven unit. Alternatively, the same functions could be controlled by timer means and variable resistor control of the magnetron and other variables described. These in turn could provide for visual readout of both the set time and the lapsed time as well as the power selected.

The use of a microprocessor however provides for further versatility, such as the ability to preset the instrument for more than one setting of time and power usage. Microprocessors presently available for such usage have a high degree of reliability and may have a longer life expectancy than mechanical controls. Further, simple microprocessors provide increased flexibility for programming at a competitive cost.

Many uses of the present invention repetitive testing of numerous nearly identical samples. Typically, such testing involves determination of solids, moisture level, volatile content etc. Such determinations involve initial weighing of the sample, heating the sample, reweighing the heated or dried sample and then calculating the percent change, weight difference etc. The weighing can conveniently be done with an electric balance. When an electric balance is used, the total analytical test can be automated by using the present invention in conjunction with an electric balance and a programmable calculator such as a Hewlett Packard HP97S or the like. Such programmable calculators can receive the electrical weight signal from the electric balance, store the information and use the stored weight in a subsequent calculation after heating and reweighing the sample. In this manner, numerous samples can be tested at the same time or in sequence with a plurality of samples being subjected to microwave heating at a given time.

Alternatively, when the oven of the present invention utilizes a microprocessor to control its functions, the electric balance can be directly interfaced with the microwave oven through its microprocessor using suitable transistor-transistor logic (TTL) interface means. The oven microprocessor can then store the weight signals and perform the desired calculations to give weight loss information as desired.

Using the programmable capacity of the preferred apparatus of the present invention, the oven can be preset to go through a sequential power change during drying for specified time periods. In a typical drying sequence to a minimum moisture value of a sample being dried, it may be desirable to preprogram the apparatus of the present invention to provide for a three-stage drying sequence. Such a sequence may be desirable particularly with samples which may otherwise rapidly deteriorate under prolonged microwave heating. Typically such a sequence would follow the program wherein stage 1 utilizes 100 percent magnetron power for a time period of two minutes, followed by a stage 2 at fifty percent power for three minutes, followed by stage 3 at 25 percent power for three minutes. Such preprogrammed sequences of three stages is readily provided by operator selection thereby providing initial high heating to bring a sample up to temperature at which volatiles begin to be removed from the sample, subsequently followed by lesser heating as the sample loses volatiles and concluding with lower heating to avoid degradation of the sample. Such sequences enable repetitive treatment of sample after sample without constant operator attention.

On completion of one series of tests, the operator can merely change the program to suit another series of tests as may be desired for different samples.

While the invention has been described more particularly with reference to the preferred embodiments of the present invention, it is recognized that variations can be made which are readily apparent to those skilled in the art. It is intended to claim the invention broadly in terms of its full novelty and unobviousness not being limited by the particular expressed mode or examples specifically described.

What is claimed is:

1. An analytical microwave apparatus that is especially suitable for laboratory heatings to digest or dry small analytical samples, which comprises a chamber, which retains microwave radiation therein except for that which exits back out through an opening in the chamber which is an entrance for such radiation, which chamber is devoid of any microwave absorbent material except for any analytical samples being heated, a magnetron located outside of such chamber, a wave guide located between the chamber and the magnetron and communicating them through the chamber opening, an isolator, comprising a magnetic shape in the wave guide, and a dummy load and a heat sink, in combination, external to such wave guide, which dummy load absorbs any microwave radiation that exits from the chamber through the wave guide, a first fan or blower for directing air past the heat sink to cool it, so that the air can cool the heat sink continuously over long time periods when the magnetron is operating at full power and there are no analytical samples in the chamber, mechanical radiation mixing means for dispersing throughout the chamber microwave radiation entering the chamber from the wave guide, a second fan or blower, of variable speed capability, for cooling the chamber by drawing air through it, and for removing from the chamber any volatiles that may be generated by the analytical samples during heating thereof, a turntable for moving analytical samples in the chamber while they are being subjected to microwave radiation therein, and programmable means for controlling power input to the magnetron and the duration of such power input, so that the analytical samples may be safely and effectively heated to digest or dry them without damaging the magnetron and without allowing escaping of microwave radiation from the analytical microwave apparatus.

2. An analytical microwave apparatus according to claim 1 wherein the turntable is of synthetic organic polymeric plastic material which is transparent to microwave radiation.

3. An apparatus according to claim 2 wherein the turntable is of polypropylene, polycarbonate, polyester or polytetrafluoroethylene.

4. An apparatus according to claim 2 wherein the turntable is of variable speed capability.

5. An apparatus according to claim 4 wherein the speed of rotation of the turntable is adjustable within the range of ½ to 20 revolutions per minute.

6. An apparatus according to claim 1 wherein the chamber includes interior walls of microwave transparent and chemically resistant material and a door interior wall of such material.

7. An apparatus according to claim 1 wherein the programmable means for controlling power input to the magnetron and for controlling the duration of such power input includes a microprocessor.

8. An apparatus according to claim 7 which comprises a digital panel readout which provides visible information about the program in operation in the apparatus.

*9. An analytical microwave apparatus that is suitable for laboratory heatings to digest or dry analytical samples, which comprises a chamber, which retains microwave radiation therein except for that which exits back out through an opening in the chamber, which is an entrance for such radiation, which chamber is devoid of any microwave absorbent material except for any analytical samples being heated, a magnetron located outside of such chamber, a wave guide located between the chamber and the magnetron and communicating them through the chamber opening, an isolator, comprising a magnetic shape in the wave guide, and a dummy load and a heat sink, in combination, external to such wave guide, which dummy load absorbs any microwave radiation that exits from the chamber through the wave guide, means for directing air past the heat sink to cool it, so that the air can cool the heat sink continuously over long time periods when the magnetron is operating at full power and there is no analytical sample in the chamber, mechanical radiation mixing means for dispersing throughout the chamber microwave radiation entering the chamber from the wave guide, a turntable for moving an analytical sample in the chamber while it is being subjected to microwave radiation therein, and programmable means for controlling power input to the magnetron and the duration of such power input, so that analytical samples may be safely and effectively heated to digest or dry them without damaging the magnetron and without allowing escaping of microwave radiation from the analytical microwave apparatus.*

*10. An analytical microwave apparatus according to claim 9 wherein the means for directing air past the heat sink to cool it is a blower.*

*11. An analytical microwave apparatus according to claim 9 wherein the means for directing air past the heat sink to cool it is a fan.*

* * * * *